US006391908B1

(12) United States Patent
Bach et al.

(10) Patent No.: US 6,391,908 B1
(45) Date of Patent: May 21, 2002

(54) OXIME AMIDE INDOLE TYPE SPLA$_2$ INHIBITORS

(75) Inventors: Nicholas James Bach; Richard Waltz Harper; Michael Dean Kinnick; Ho-Shen Lin, all of Indianapolis; John Michael Morin, Jr., Brownsburg; Michael Enrico Richett, Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/856,942
(22) PCT Filed: Dec. 20, 1999
(86) PCT No.: PCT/US99/30405
§ 371 Date: May 30, 2001
§ 102(e) Date: May 30, 2001
(87) PCT Pub. No.: WO00/37358
PCT Pub. Date: Jun. 29, 2000

Related U.S. Application Data
(60) Provisional application No. 60/113,303, filed on Dec. 22, 1998.

(51) Int. Cl.$^7$ .................. A61K 31/404; C07D 209/22
(52) U.S. Cl. ........................ 514/419; 548/495
(58) Field of Search ..................... 548/495; 514/419

(56) References Cited

U.S. PATENT DOCUMENTS 5,238,938 A     8/1993    Tone et al. ................ 514/253

*Primary Examiner*—Laura L. Stockton
(74) *Attorney, Agent, or Firm*—Roger S. Benjamin

(57) ABSTRACT

A class of novel oxime indoles is disclosed together with the use of such compounds for inhibiting sPLA$_2$ mediated release of fatty acids for treatment of inflammatory diseases such as septic shock.

19 Claims, No Drawings

OXIME AMIDE INDOLE TYPE SPLA₂ INHIBITORS

This application is a 371 of PCT/US99/30405 filed Dec. 20, 1999 which claims the benefit of U.S. Provisional application No. 60/113,303 filed Dec. 22, 1998.

FIELD OF THE INVENTION

This invention relates to novel indole compounds useful for inflammatory diseases.

BACKGROUND OF THE INVENTION

The structure and physical properties of human non-pancreatic secretory phospholipase $A_2$ (hereinafter called, "$sPLA_2$") has been thoroughly described in two articles, namely, "Cloning and Recombinant Expression of Phospholipase $A_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase $A_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that $sPLA_2$ is a rate limiting enzyme in the arachidonic acid cascade which hydrolyzes membrane phospholipids. Thus, it is important to develop compounds which inhibit $sPLA_2$ mediated release of fatty acids (e.g., arachidonic acid). Such compounds would be of value in general treatment of conditions induced and/or maintained by overproduction of $sPLA_2$; such as sepsis or rheumatoid arthritis.

It is desirable to develop new compounds and treatments for $sPLA_2$ induced diseases.

SUMMARY OF THE INVENTION

This invention is a novel class of indole oxime amide compounds having potent and selective effectiveness as inhibitors of mammalian $sPLA_2$.

This invention is also the use of indole oxime amide compounds in the treatment and prevention of Inflammatory Diseases.

This invention is also the use of novel of indole oxime amide compounds to inhibit,mammalian $sPLA_2$ mediated release of fatty acids.

This invention is also a pharmaceutical compositions containing indole oxime amide compounds of the invention.

Definitions

The term, "Inflammatory Diseases" refers to diseases such as inflammatory bowel disease, sepsis, septic shock, adult respiratory distress syndrome, pancreatitis, trauma-induced shock, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit $sPLA_2$ mediated release of fatty acid and to thereby inhibit or prevent the arachidonic acid cascade and its deleterious products.

The term, "indole nucleus" refers to a nucleus (having numbered positions)with the structural formula (X):

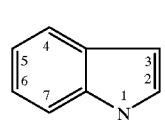

(X)

The indole compounds of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo.

The term, heterocyclic radical, refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl. phenylpyridinyl, benzylpyridinyl, pyrimidinyl, phenylpyrimidinyl, pyrazinyl, 1,3,5-triazinyl, quinolinyl, phthalazinyl, quinazolinyl,morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiopheneyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, spiro[5.5]undecanyl, naphthyl, norbornanyl, bicycloheptadienyl, tolulyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (a):

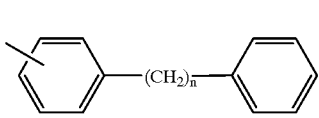

(a)

where n is a number from 1 to 8.

The term, "non-interfering substituent", refers to radicals suitable for substitution at positions 4,5,6 and/or 7 of the indole nucleus and on other nucleus substituents (as hereinafter described for Formula I), and radicals suitable for substitution on the heterocyclic radical and carbocyclic radical as defined above. Illustrative non-interfering radicals are $C_1$–$C_8$ alkyl, $C_2$–$C_8$ alkenyl, $C_2$–$C_8$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_8$ alkoxy, $C_2$–$C_8$ alkenyloxy, $C_2$–$C_8$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_8$ alkylsulfinyl, $C_1$–$C_8$ alkylsulfonyl, $C_2$–$C_8$ haloalkoxy, $C_1$–$C_8$ haloalkylsulfonyl, $C_2$–$C_8$ haloalkyl, $C_1$–$C_8$ hydroxyalkyl, —C(O)O($C_1$–$C_8$ alkyl), —(CH$_2$)$_n$—O—($C_1$–$C_8$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and carbonyl; where n is from 1 to 8.

The term, "organic substituent" refers to a monovalent radical consisting of carbon and hydrogen with or without oxygen, nitrogen, sulfur, halogen, or other elements. Illustrative organic substituents are $C_1$–$C_8$ alkyl, aryl, $C_7$–$C_{14}$ aralkyl, $C_7$–$C_{14}$ alkaryl, $C_3$–$C_8$ cycloalkyl, $C_1$–$C_8$ alkoxyalkyl and these groups substitued with halogen, —CF$_3$, —OH, $C_1$–$C_8$ alkyl, amino, carbonyl, and —CN.

The term, "acylsulfonamide group" is an (acidic group) represented by the formula:

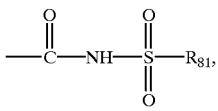

where $R_{81}$ is an organic substituent or the radical—CF$_3$.

The term "substituted group" is an organic group substituted with one or more non-interfering substituents.

The term, "(acidic group)" means an organic group which when attached to an indole nucleus, through suitable linking atoms (hereinafter defined as the "acid linker"), acts as a proton donor capable of hydrogen bonding. Illustrative of an (acidic group) are the following:

-5-tetrazolyl,

—SO$_3$H,

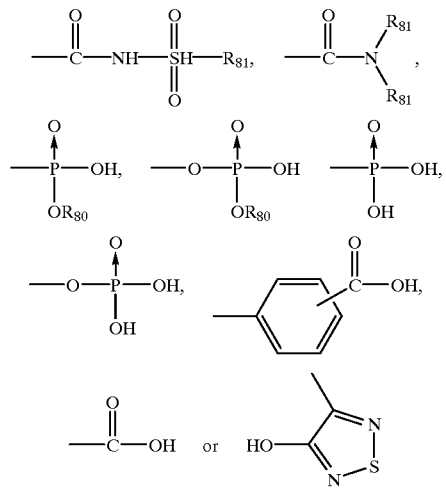

where n is 1 to 8, $R_{80}$ is a metal or $C_1$–$C_8$ and $R_{81}$ is an organic substituent or —CF$_3$.

The words, "acid linker" refer to a divalent linking group symbolized as, —(L$_a$)—, which has the function of joining the 4 or 5 position of the indole nucleus to an acidic group in the general relationship:

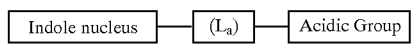

The words, "acid linker length", refer to the number of atoms (excluding hydrogen) in the shortest chain of the linking group —(L$_a$)— that connects the 4 or 5 position of the indole nucleus with the acidic group. The presence of a carbocyclic ring in —(L$_a$)— counts as the number of atoms approximately equivalent to the calculated diameter of the carbocyclic ring. Thus, a benzene or cyclohexane ring in the acid linker counts as 2 atoms in calculating the length of —(L$_a$)—. Illustrative acid linker groups are;

(a)

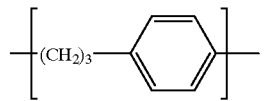

(b)

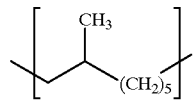

(c)

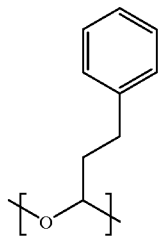

wherein, groups (a), (b), and (c) have acid linker lengths of 5, 7, and 2, respectively.-

The term, "amine", includes primary, secondary and tertiary amines.

The terms, "mammal" and "mammalian" include human.

The term, "alkylene chain of 1 or 2 carbon atoms" refers to the divalent radicals, —CH$_2$—CH$_2$— and —CH$_2$—.

The term, "group containing 1 to 4 non-hydrogen atoms" refers to relatively small groups which form substituents at the 2 position of the indole nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —CF$_3$, —Cl, —Br, —NO$_2$, —CN, —SO$_3$; and (ii) groups having hydrogen atoms which contain less than 4 non-hydrogen atoms such as —CH$_3$, —C$_2$H$_5$, and —CH=CH$_2$.

The term "oxime amide" means the radical, —C=NOR—C(O)NH$_2$.

The term "thio-oxime amide" means the radical —C=NOR—C(S)—NH$_2$.

The term "spiro[5.5]undecanyl" refers to the group represented by the formula;

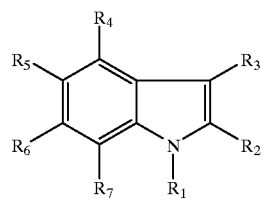

The Indole Compounds of the Invention

The compounds of the invention have the general formula (I) or a pharmaceutically acceptable salt, solvate or prodrug thereof;

(I)

wherein $R_1$ is selected from groups (a), (b) and (c) wherein;
  (a) is C$_7$–C$_{20}$ alkyl, C$_7$–C$_{20}$ haloalkyl, C$_7$–C$_{20}$ alkenyl, C$_7$–C$_{20}$ alkynyl, carbocyclic radical, or heterocyclic radical, or
  (b) is a member of (a) substituted with one or more independently selected non-interfering substituents; or
  (c) is the group —(L$_1$)—R$_{11}$; where, —(L$_1$)— is a divalent linking group of 1 to 8 atoms and where R$_{11}$ is a group selected from (a) or (b);

$R_2$ is hydrogen, or a group containing 1 to 4 non-hydrogen atoms plus any required hydrogen atoms;

$R_3$ is —(L$_3$)—Z, where —(L$_3$)— is a divalent linker group selected from a bond or a divalent group selected from:

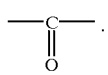

and Z is selected from an oxime amide or oxime thioamide group represented by the formulae,

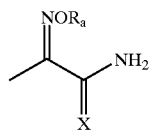

wherein, X is oxygen or sulfur; and R$_a$ is selected from hydrogen, C$_1$–C$_8$ alkyl, aryl, C$_1$–C$_8$ alkaryl, C$_1$–C$_8$ alkoxy, aralkyl and —CN;

$R_4$ and $R_5$ are independently selected from hydrogen, a non-interfering substituent, or the group, —(L$_a$)-(acidic group); wherein —(L$_a$)—, is an acid linker having an acid linker length of 1 to 8, provided, that at least one of R$_4$ and R$_5$ must be the group, —(L$_a$)— (acidic group);

$R_6$ and $R_7$ are selected from hydrogen, non-interfering substituent, carbocyclic radical, carbocyclic radical substituted with non-interfering substituent(s), heterocyclic radicals, and heterocyclic radical substituted with non-interfering substituent(s).

Preferred Subgroups of Compounds of Formula (I)

I. Preferred $R_1$ Substituents

A preferred subclass of compounds of formula (I) are those where for $R_1$ the divalent linking group —(L$_1$)— is a group represented by any one of the following formulae (Ia), (Ib), (Ic), (Id), (Ie), or (If):

(Ia)

(Ib)

(Ic)

(Id)

(Ie)

(If)

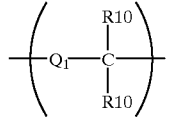

where $Q_1$ is a bond or any of the divalent groups (Ia), (Ib), (Ic), (Id), (Ie), and (If) and each $R_{10}$ is independently hydrogen, C$_{1-8}$ alkyl, C$_{1-8}$ haloalkyl or C$_{1-8}$ alkoxy.

Particularly preferred as the linking group —(L$_1$)— of R$_1$ is an alkylene chain of 1 or 2 carbon atoms, namely, —(CH$_2$)— or —(CH$_2$—CH$_2$)—.

The preferred group for $R_{11}$ is a substituted or unsubstituted group selected from the group consisting of C$_5$–C$_{14}$ cycloalkyl, C$_5$–C$_{14}$ cycloalkenyl, phenyl, naphthyl, norbornanyl, bicycloheptadienyl, tolulyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (a);

(a)

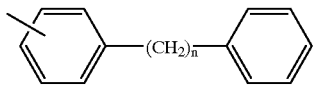

where n is a number from 1 to 8.

Particularly preferred are compounds wherein for $R_1$ the combined group —($L_1$)—$R_{11}$ is selected from the group consisting of

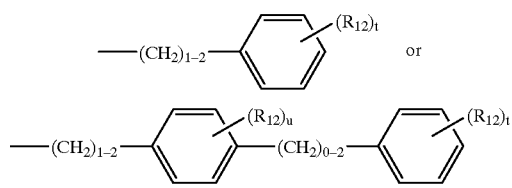

where $R_{12}$ is a radical independently selected from halo, $C_1$–$C_8$ alkyl, $C_1$–$C_8$ alkoxy, —S—($C_1$–$C_8$ alkyl), —O—($C_1$–$C_8$ alkyl) and $C_1$–$C_8$ haloalkyl where t is a number from 0 to 5 and u is a number from 0 to 4.

II. Preferred $R_2$ Substituents $R_2$ is preferably selected from the group consisting of hydrogen, $C_1$–$C_4$ alkyl, $C_2$–$C_4$ alkenyl, —O—($C_1$–$C_3$ alkyl), —S—($C_1$–$C_3$ alkyl), —$C_3$–$C_4$ cycloalkyl —$CF_3$, halo, —$NO_2$, —CN, —$SO_3$. Particularly preferred $R_2$ groups are selected from hydrogen, methyl, ethyl, propyl, isopropyl, cyclopropyl, —F, —$CF_3$, —Cl, —Br, or —O—$CH_3$.

III. Preferred $R_3$ Substituents

A preferred subclass of compounds of formula (I) are those wherein X is oxygen.

Another preferred subclass of compounds of formula (I) are those wherein Z is a oxime amide group.

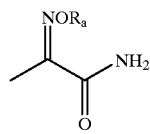

Most preferred are compounds of formula (I) wherein $R_3$ is an oxime amide group and $R_a$ is hydrogen, methyl or ethyl. For the group $R_3$ it is preferred that the linking group —($L_3$)— be a bond.

IV. Preferred $R_4$ Substituents

Another preferred subclass of compounds of formula (I) are those wherein $R_4$ is a substituent having an acid linker with an acid linker length of 2 or 3 and the acid linker group, —($L_4$)—, for $R_4$ is selected from a group represented by the formula;

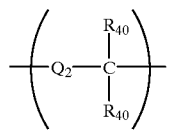

where $Q_2$ is selected from the group —($CH_2$)—, —O—, —NH—, —C(O)—, and —S—, and each $R_{40}$ is independently selected from hydrogen, $C_1$–$C_8$ alkyl, aryl, $C_1$–$C_8$ alkaryl, $C_1$–$C_8$ alkoxy, aralkyl, and halo. Most preferred are compounds where the acid linker, —($L_4$)—, for $R_4$ is selected from the specific groups;

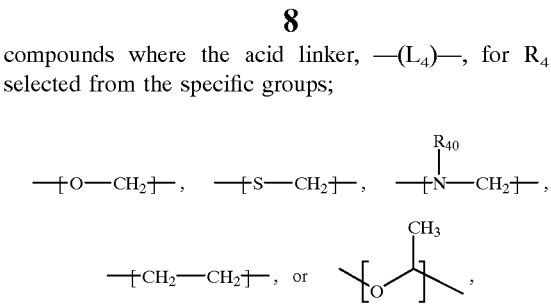

where $R_{40}$ is hydrogen or $C_1$–$C_8$ alkyl. Preferred as the (acidic group) in the group $R_4$ are acidic groups selected from:

-5-tetrazolyl,

—$SO_3H$,

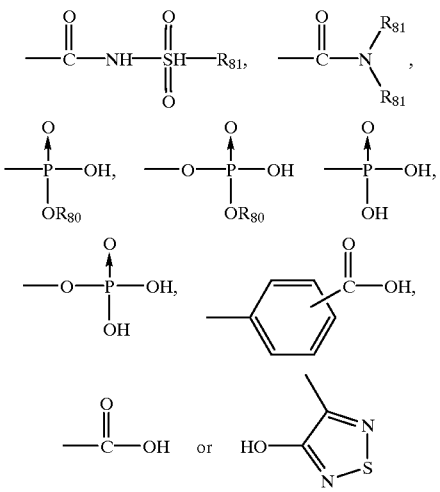

where $R_{80}$ is a metal or $C_1$–$C_8$ and $R_{81}$ is an organic substituent or —$CF_3$. A salt or a prodrug derivative of the (acidic group) is also a suitable substituent.

Particularly preferred are acidic groups selected from:

—$CO_2H$, —$SO_3H$, —$P(O)(OH)_2$, or salt, and prodrug (e.g., ester, amide) derivatives thereof. The most preferred acidic group in the compounds of the invention is a carboxylic acid group, —$CO_2H$.

V. Preferred $R_5$ Substituents

Preferred acid linker, —($L_a$)—, for $R_5$ is selected from the group consisting of;

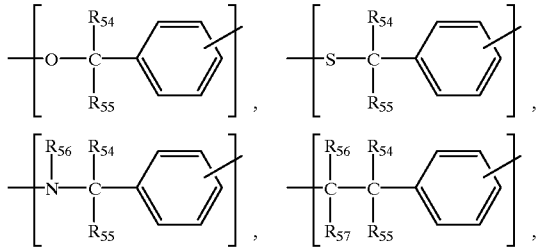

-continued

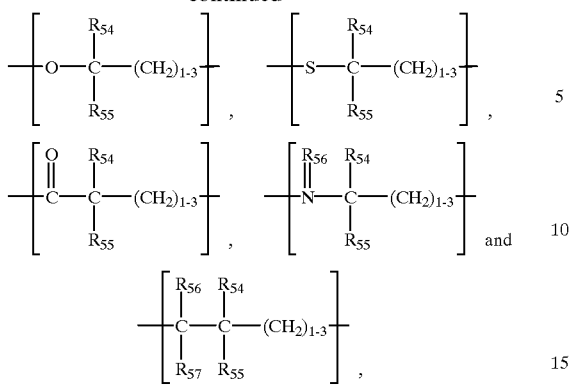

wherein $R_{54}$, $R_{55}$, $R_{56}$ and $R_{57}$ are each independently hydrogen, $C_1-C_8$ alkyl, $C_1-C_8$ haloalkyl, aryl, $C_1-C_8$ alkoxy, or halo.

VI. Preferred (Acidic Group) for $R_4$ and/or $R_5$ Substitutions

At least one of $R_4$ and $R_5$ must be the group, —$(L_a)$— (acidic group). The preferred (acidic group) on the group —$(L_a)$-(acidic group) of $R_4$ or $R_5$ is selected from —$CO_2H$, —$SO_3H$, or —$P(O)(OH)_2$. In addition, it is preferred that only one $R_4$ or $R_5$ substituents be the group, —$(L_a)$-(acidic group).

The preferred (acidic group) is the same as those set out in the prior section describing $R_4$ substituents.

V. Preferred $R_6$ Substituents

Another preferred subclass of compounds of formula (I) are those wherein for $R_6$ the non-interfering substituent is methyl, ethyl, propyl, isopropyl, thiomethyl, —O-methyl, $C_4-C_6$ alkyl, $C_2-C_6$ alkenyl, $C_2-C_6$ alkynyl, $C_7-C_{12}$ aralkyl, $C_7-C_{12}$ alkaryl, $C_3-C_8$ cycloalkyl, $C_3-C_8$ cycloalkenyl, phenyl, tolulyl, xylenyl, biphenyl, $C_1-C_6$ alkoxy, $C_2-C_6$ alkenyloxy, $C_2-C_6$ alkynyloxy, $C_2-C_{12}$ alkoxyalkyl, $C_2-C_{12}$ alkoxyalkyloxy, $C_2-C_{12}$ alkylcarbonyl, $C_2-C_{12}$ alkylcarbonylamino, $C_2-C_{12}$ alkoxyamino, $C_2-C_{12}$ alkoxyaminocarbonyl, $C_1-C_{12}$ alkylamino, $C_1-C_6$ alkylthio, $C_2-C_{12}$ alkylthiocarbonyl, $C_1-C_6$ alkylsulfinyl, $C_1-C_6$ alkylsulfonyl, $C_2-C_6$ haloalkoxy, $C_1-C_6$ haloalkylsulfonyl, $C_2-C_6$ haloalkyl, $C_1-C_6$ hydroxyalkyl, —$C(O)O(C_1-C_6$ alkyl), —$(CH_2)_n$—O—$(C_1-C_6$ alkyl), benzyloxy, phenoxy, phenylthio, —$(CONHSO_2R)$, —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and carbonyl; where n is from 1 to 8.

Most preferred as non-interfering substituents are methyl, ethyl, propyl, and isopropyl.

Preferred compounds of the invention are those having the general formula (II), or a pharmaceutically acceptable salt, solvate or prodrug derivative thereof;

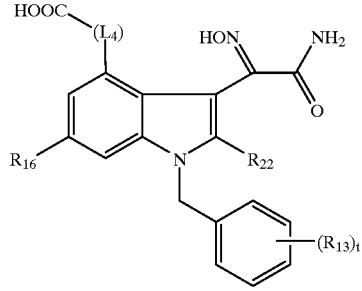

wherein;

$R_{22}$ is selected from hydrogen, methyl, ethyl, propyl, isopropyl, cyclopropyl, —F, —$CF_3$, —Cl, —Br, or —O—$CH_3$;

—$(L_4)$— is a divalent group selected from;

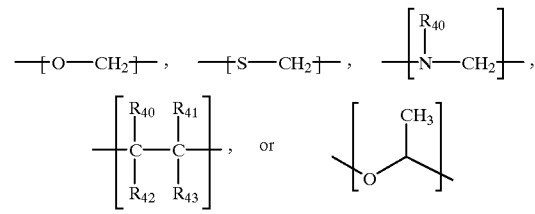

where $R_{40}$, $R_{41}$, $R_{42}$, and $R_{43}$ are each independently selected from hydrogen or $C_1-C_8$ alkyl.

$R_{16}$ is selected from hydrogen, $C_1-C_8$ alkyl, $C_1-C_8$ alkoxy, $C_1-C_8$ alkylthio $C_1-C_8$ haloalkyl, $C_1-C_8$ hydroxyalkyl, and halo.

$R_{13}$ is selected from hydrogen and $C_1-C_8$ alkyl, $C_1-C_8$ alkoxy, —S—$(C_1-C_8$ alkyl), $C_1-C_8$ haloalkyl, $C_1-C_8$, phenyl, halophenyl, hydroxyalkyl, and halo, and t is an integer from 0 to 5.

Preferred specific compounds (and all pharmaceutically acceptable salts, solvates and prodrug derivatives thereof) which are illustrative of the compounds of the invention are as follow:

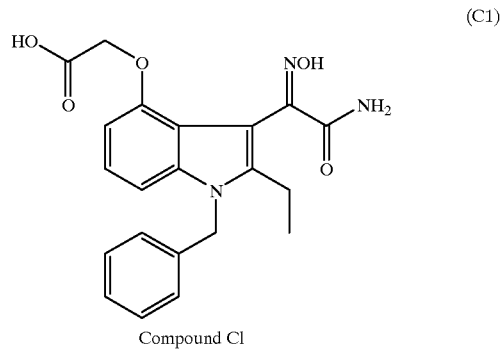

Compound C1

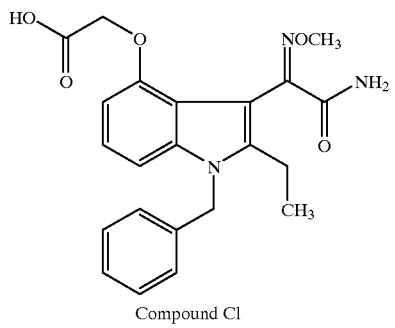

Compound Cl

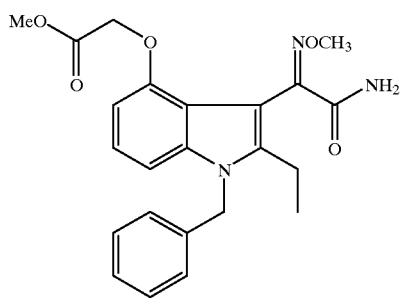

The salts of the above indole compounds represented by formulae (I) and (II) are an additional aspect of the invention. In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin. For example, the (acidic group) of the substituent $R_4$ of Formula I may be selected as —$CO_2H$ and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," J. Phar. Sci., 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of diastereomers and diastereomers, because they have different melting points, different boiling points, and different solubilities can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula (I) (in a medium such as dimethylformamide) 4-(2-chloroethyl) morpholine hydrochloride (available from Aldrich Chemical Co., Milwaukee, Wis. USA, Item No. C4,220-3).

Method of Making the Compounds of the Invention

The synthesis of the indole compounds of the invention (viz., Compounds of Formulae I and II) can be accomplished by well known methods as recorded in the chemical literature. In particular, the indole starting materials may be prepared by the synthesis schemes taught in U.S. Pat. No. 5,654,326; the disclosure of which is incorporated herein by reference. Another method of making 1H-indole-3-glyoxylamide sPLA$_2$ inhibitors is described in U.S. patent application Ser. No. 09/105381, filed Jun. 26, 1998 and titled, "Process for Preparing 4-substituted 1-H-Indole-3-glyoxyamides" the entire disclosure of which is incorporated herein by reference.

U.S. patent application Ser. No. 09/105381 discloses the following process having steps (a) thru (i):

Preparing a compound of the formula (IZ) or a pharmaceutically acceptable salt or prodrug derivative thereof

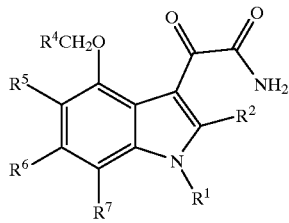
(IZ)

wherein:
R¹ is selected from the group consisting of —C₇–C₂₀ alkyl,

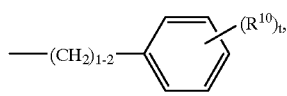

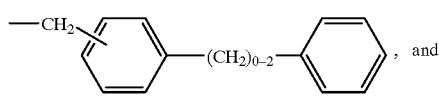, and

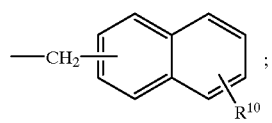;

where
R¹⁰ is selected from the group consisting of halo, $C_1$–$C_{10}$ alkyl, $C_1$–$C_{10}$ alkoxy, —S—($C_1$–$C_{10}$ alkyl) and halo ($C_1$–$C_{10}$)alkyl, and t is an integer from 0 to 5 both inclusive;
R² is selected from the group consisting of hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), aryl, aryloxy and HET;
R⁴ is selected from the group consisting of —CO₂H, —SO₃H and —P(O)(OH)₂ or salt and prodrug derivatives thereof; and
R⁵, R⁶ and R⁷ are each independently selected from the group consisting of hydrogen, ($C_1$–$C_6$)alkyl, ($C_1$–$C_6$) alkoxy, halo($C_1$–$C_6$)alkoxy, halo($C_2$–$C_6$)alkyl, bromo, chloro, fluoro, iodo and aryl;
which process comprises the steps of:
a) halogenating a compound of formula X

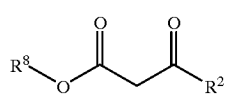
X where R⁸ is ($C_1$–$C_6$)alkyl, aryl or HET; with SO₂Cl₂ to form a compound of formula

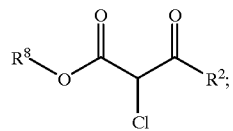
IX b) hydrolyzing and decarboxylating a compound of formula IX

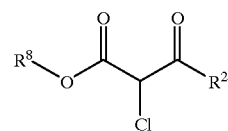
IX to form a compound of formula VIII

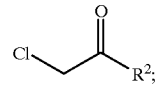
VIII c) alkylating a compound of formula VII

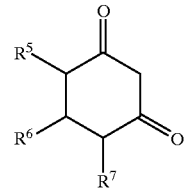
VII with a compound of formula VIII

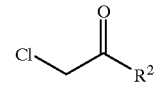
VIII to form a compound of formula VI

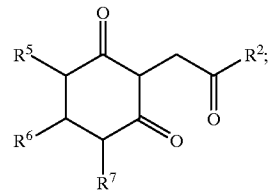
VI d) aminating and dehydrating a compound of formula VI

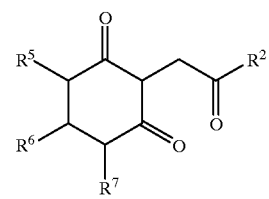
VI with an amine of the formula R¹NH₂ in the presence of a solvent that forms and azeotrope with water to form a compound of formula V;

e) oxidizing a compound of formula V

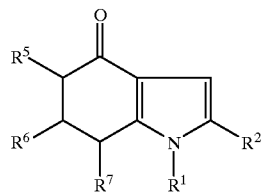

V by refluxing in a polar hydrocarbon solvent having a boiling point of at least 150° C. and a dielectric constant of at least 10 in the presence of a catalyst to form a compound of formula IV

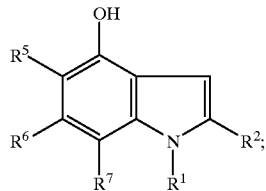

IV f) alkylating a compound of the formula IV

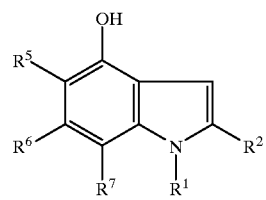

IV with an alkylating agent of the formula $XCH_2R^{4a}$ where X is a leaving group and $R^{4a}$ is $—CO_2R^{4b}$, $—SO_3R^{4b}$, $—P(O)(OR^{4b})_2$, or $—P(O)(OR^{4b})H$, where $R^{4b}$ is an acid protecting group to form a compound of formula III

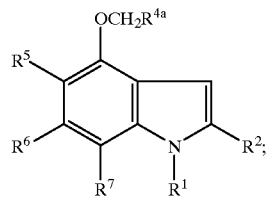

III g) reacting a compound of formula III

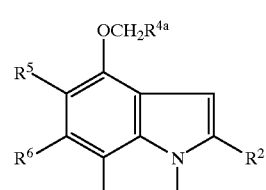

III with oxalyl chloride and ammonia to form a compound of formula IIZ

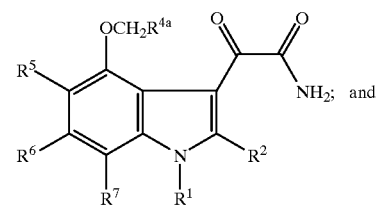

IIZ h) optionally hydrolyzing a compound of formula IIZ

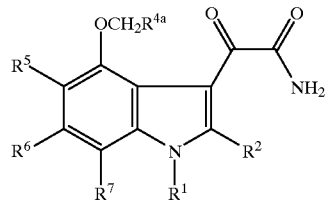

IIZ to form a compound of formula I.

Other synthesis procedures useful for the synthesis of the starting material are shown in the Scheme below:

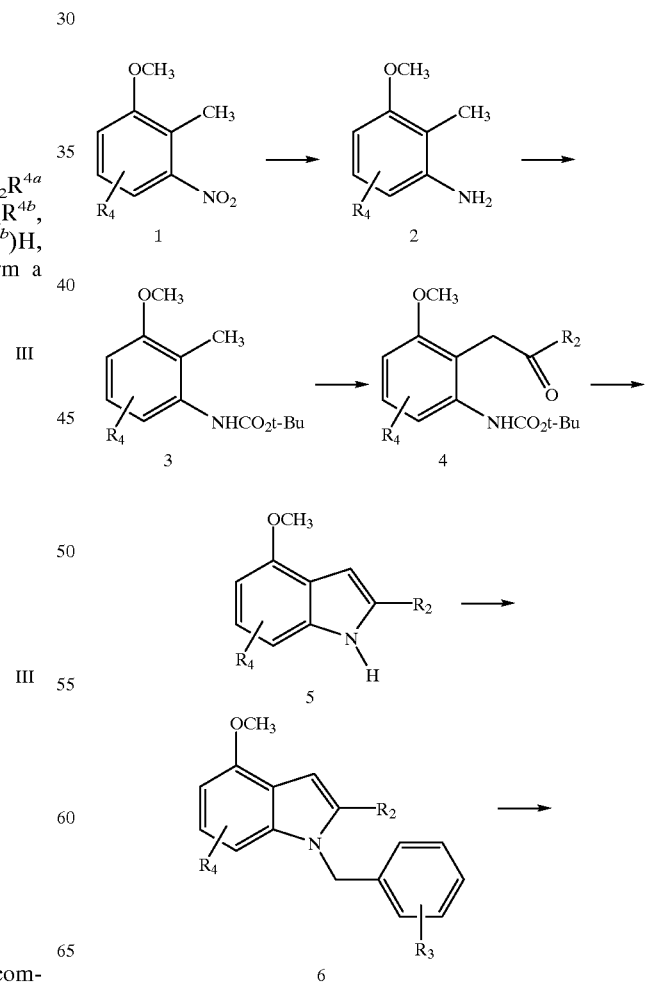

17
-continued

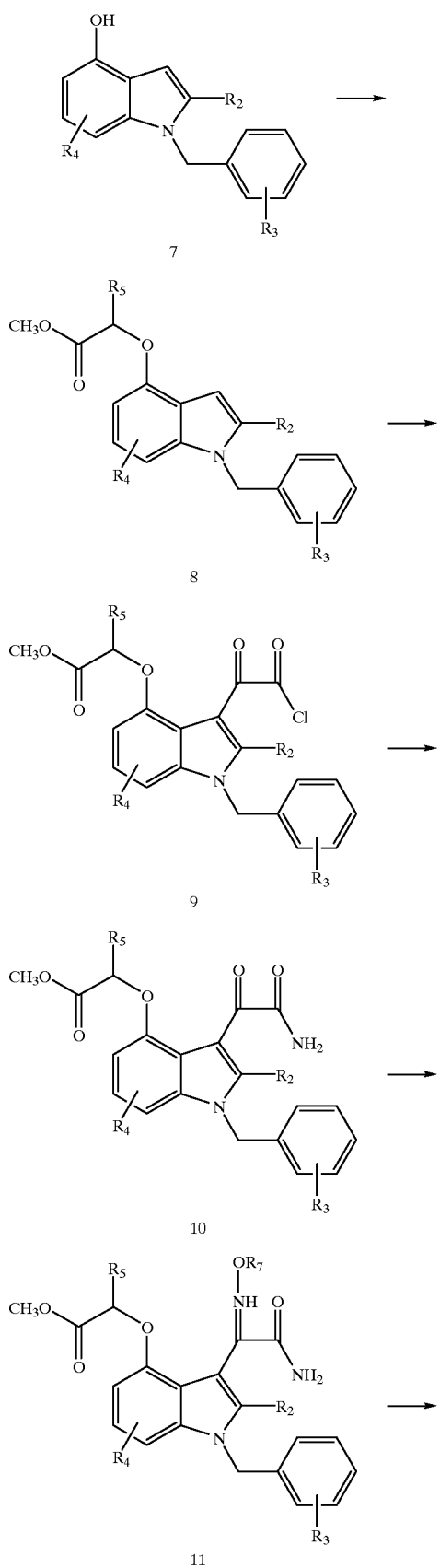

18
-continued

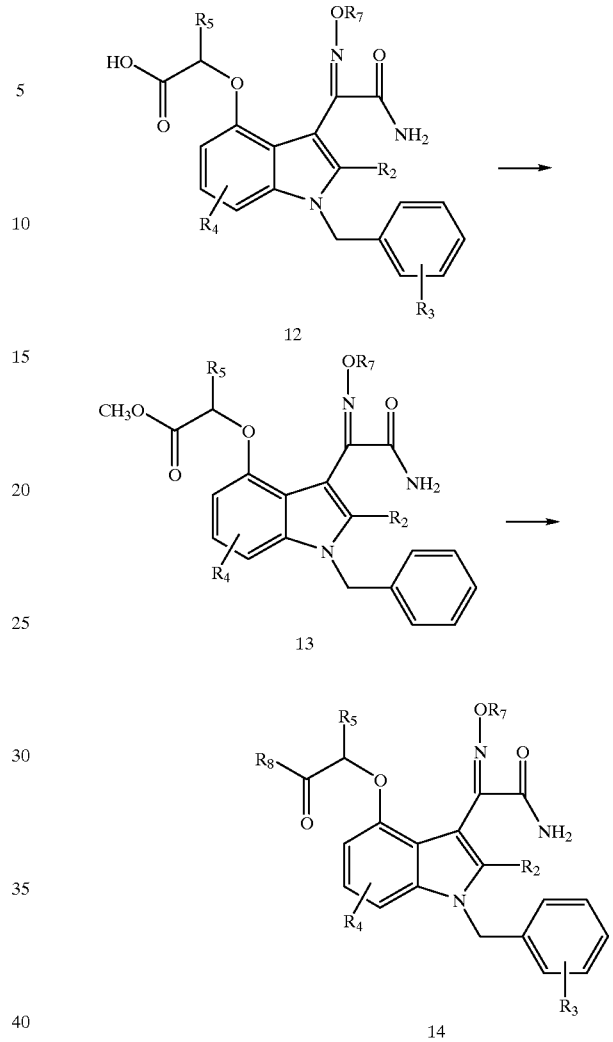

Synthesis of the Compounds of the Invention

The synthesis of indole oxime amides (compound of formula I, supra.) of this invention uses as starting material ((3-(2-amino-1,2-dioxoethyl)-2-methyl-1-(phenylmethyl)-1H-indol-4-yl)oxy)acetic acid (glyoxylamide), or a salt thereof (compound of formula II, supra.). This starting material may be prepared by the reaction schemes or method of Example 1 of U.S. Pat. No. 5,654,326, (the disclosure of which is incorporated herein by reference). Similar methods are shown in European Patent Application No. 95302166.4, Publication No. 0 675 110 (publ., Oct. 4, 1995). Other conventional methods may also be used for preparing the starting material.

To obtain the 3-oxime amide-1H-indole compounds substituted in the 4-position with an (acidic group) linked through an oxygen atom, the reactions outlined in the scheme supra, are used (for conversions 1 through 5, see ref. Robin D. Clark, Joseph M. Muchowski, Lawrence E. Fisher, Lee A. Flippin, David B. Repke, Michel Souchet, *Synthesis*, 1991, 871–878, the disclosures of which are incorporated herein by reference). The starting material ortho-nitrotoluene, 1, is readily reduced to 2-methyl, 3-metoxyaniline, 2. Reduction of 1 is by the catalytic hydrogenation of the corresponding nitrotoluene using palladium on carbon as catalyst. The reduction can be carried out in ethanol or tetrahydrofuran (THF) or a combination of both, using a low pressure of hydrogen. The aniline, 2, obtained, is converted to the N-tert-butyloxycarbonyl derivative, 3, in good yield, on heating with di-tert-butyl dicarbonate in THF at reflux temperature. The dilithium salt of the dianion of 3 is generated at −40 to −20° C. in THF using sec-butyllithium and reacted with the appropriately substituted N-methoxy-N-methylalkanamide to form the ketone 4. This product (4) may be purified by crystallization from hexane, or reacted directly with trifluoroacetic acid in methylene chloride to give the 1,3-unsubstituted indole 5. The 1,3-unsubstituted indole 5 is reacted with sodium hydride in dimethylformamide at room temperature (20–25° C.) for 0.5–1.0 hour. The resulting sodium salt of 5 is treated with an equivalent of arylmethyl halide and the mixture stirred at a temperature range of 0–100° C., usually at ambient room temperature, for a period of 4 to 36 hours to give the 1-arylmethylindole, 6. This indole, 6, is O-demethylated by stirring with boron tribromide in methylene chloride for approximately 5 hours (see ref. Tsung-Ying Shem and Charles A Winter, *Adv. Drug Res.*, 1977, 12, 176, the disclosure of which is incorporated herein by reference).

Compounds substituted at the 5 position of the indole nucleus with an (acidic group) may be prepared by methods and starting materials shown in schemes 2 and 3 of U.S. Pat. No. 5,654,326; the disclosure of which is incorporated herein by reference.

To introduce the oxime functionality, the methyl ester of the glyoxylamide (compound 10 in the scheme supra.) is heated with hydroxylamine hydrochloride (when $R_7$ is H) in a THF/methanol mixture for 8 hours or until the reaction was deemed complete. The reaction product was isolated by chromatography or other known laboratory procedure to afford a white solid in high yield. Substituted oximes such as when $R_7$ is methyl, ethyl, phenyl or other substituent can be prepared by reacting the corresponding substituted hydroxylamine hydrochloride or free base with the glyoxylamide as described supra. The ester functionality at the 4 or 5 position on the indole nucleus can be: (1) converted to the acid by hydrolysis using lithium hydroxide or other known ester hydrolysis methods or (2) to an amide functionality directly or via the acid functionality. The oxime thioamide analogs of the compounds of this invention can be made by substituting trimethylsilylisothiocyanate for trimethylsilyisocyante to produce the oxime thioamide analog of compound 10, which can hydrolyzed to the oxime thioamide-indole analog of compound 11. The oxime amides as well as the oxime thioamide compounds can also be isolated as the free acid or as its sodium salt.

Methods of Using the Compounds of the Invention

The indole compounds described herein are believed to achieve their beneficial therapeutic action principally by direct inhibition of mammalian (including human) $sPLA_2$, and not by acting as antagonists for arachidonic acid, nor other active agents below arachidonic acid in the arachidonic acid cascade, such as 5-lipoxygenases, cyclooxygenases, and etc.

The method of the invention for inhibiting $sPLA_2$ mediated release of fatty acids comprises contacting mammalian $sPLA_2$ with an therapeutically effective amount of indole compounds corresponding to Formulae (I) or (II) as described herein including salt or a prodrug derivative thereof.

Another aspect of this invention is a method for treating Inflammatory Diseases such as inflammatory bowel disease, septic shock, adult respiratory distress syndrome, panceatitis, trauma, bronchial asthma, allergic rhinitis, rheumatoid arthritis, osteoarthritis, and related diseases which comprises administering to a mammal (including a human) a therapeutically effective dose of the indole compound of the invention (see, formulae I and II).

As previously noted the compounds of this invention are useful for inhibiting $sPLA_2$ mediated release of fatty acids such as arachidonic acid. By the term, "inhibiting" is meant the prevention or therapeutically significant reduction in release of $sPLA_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably compounds of the invention (per Formula I or II) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the indole compound of the invention together with a pharmaceutically acceptable carrier or diluent therefor. The present pharmaceutical formulations are prepared by known procedures using well known and readily available ingredients.

In making the compositions of the present invention, the Active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets the Active ingredient is mixed with a carrier having the necessary binding properties in suitable proportions and compacted in the shape and size desired. The powders and tablets preferably contain from about 1 to about 99 weight percent of the Active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active ingredient can be dissolved or suspended in a pharmaceutically acceptable carrier, such as sterile water, sterile organic solvent or a mixture of both. The Active ingredient can often be dissolved in a suitable organic solvent, for instance aqueous propylene glycol. Other compositions can be made by dispersing the finely divided Active ingredient in aqueous starch or sodium carboxymethyl cellulose solution or in a suitable oil.

The following pharmaceutical formulations 1 thru 8 are illustrative only and are not intended to limit the scope of the invention in any way. "Active ingredient", refers to a compound according to Formula (I) or (II) or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The Active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active ingredient, are made as follows:

| Active ingredient | 225 mg |
|---|---|
| Saturated fatty acid glycerides | 2,000 mg |
| Total | 2,225 mg |

The Active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

All of the products of the Examples described below as well as intermediates used in the following procedures showed satisfactory nmr and IR spectra. They also had the correct mass spectral values.

EXAMPLE 1

2-[[3-[[2-(Aminooxo)-1-(N-hydroxyimino)ethyl]-2-ethyl-1-(phenylmethyl)-1H-indol-4-yl]oxy]acetic acid

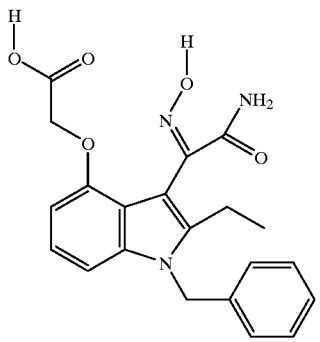

3A

A. Preparation of 2-[[3-[[2-(Aminooxo)-1-(N-hydroxyimino)ethyl]-2-ethyl-1-(phenylmethyl)-1H-indol-4-yl]oxy]acetic acid methyl ester

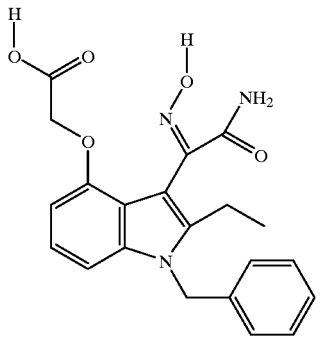

2A

A stirred mixture of 1 (600 mg, 1.52 mmol) and hydroxylamine hydrochloride (528 mg, 7.60 mmol) in THF (4 mL)/CH$_3$OH (4 mL) was heated at 55° C. for 8 h. After concentration at ambient temperature, the residue was chromatographed on silica (gradient 0–40% EtOAc in CH$_2$Cl$_2$) to give the title compound 2A (285 mg) as a white solid in 46% yield. IR (CHCl$_3$) 3510, 3415, 1757, 1667 cm$^{-1}$; $^1$H-NMR (CDCl$_3$) δ1.17 (t, J=7.5 Hz, 3H), 2.84 (q, J=7.5 Hz, 2H), 3.81 (s, 3H), 4.73 (s, 2H), 5.36 (s, 2H), 5.67 (br s, 1H), 6.31 (br s, 1H), 6.41 (d, J=7.8 Hz, 1H), 6.87 (d, J=8.2 Hz, 1H), 6.98–7.07 (m, 3H), 7.23–7.32 (m, 3H); ESIMS m/e 410 (M$^+$+1).

Elemental Analyses for C$_{22}$H$_{23}$N$_3$O$_5$.0.30(H$_2$O): Calculated: C, 63.70; H, 5.73; N, 10.13; Found: C, 63.68; H, 5.62; N, 10.20.

B. Preparation of 2-[[3-[[2-(Aminooxo)-1-(N-hydroxyimino)ethyl]-2-ethyl-1-(phenylmethyl)-1H-indol-4-yl]oxy]acetic acid

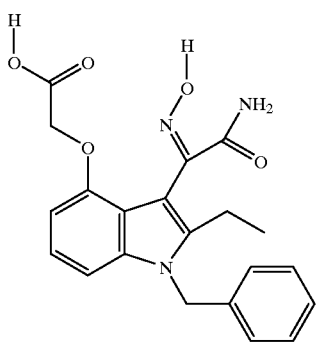

3A

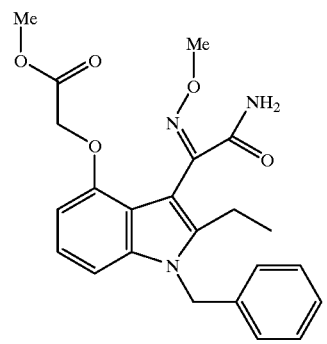

2B

Lithium hydroxide (4.17 N, 45.7 μL, 0.191 mmol) and water (0.5 mL) were added to a stirred solution of 2A (52.0 mg, 0.127 mmol) in THF (2 mL)/CH$_3$OH (2 mL). The mixture was stirred for 1.5 h to form a white suspension. THF (2 mL) was added to the suspension before it was treated with 5N HCl (50.8 μL, 0.254 mmol) to form a clear solution. After organic solvents were evaporated, the wet solid residue was filtered, washed with water and dried to give the title compound 3A (50.0 mg) as a white solid in 100% yield. IR (CHCl$_3$) 3475, 3425, 3366, 1703, 1634 cm$^{-1}$; $^1$H-NMR (DMSO-d$_6$) δ0.90–1.10 (m, 3H), 2.45–2.80 (m, 2H), 4.53 and 4.66 (both s, 2H), 5.39 (s, 2H), 6.30–6.50 (m, 1H), 6.84–7.00 (m, 4H), 7.10–7.55 (m, 5H), .11.32 and 11.38 (both s, 1H), 12.80 (br s, 1H); ESIMS m/e 396 (M$^+$+1).

Elemental Analyses for C$_{21}$H$_{21}$N$_3$O$_5$.0.40(H$_2$O): Calculated: C, 62.65; H, 5.46; N, 10.44; Found: C, 62.73; H, 5.34; N, 10.35.

EXAMPLE 2

2-[[3-[[2-(Aminooxo)-1-(N-methyloxyimino)]ethyl]-2-ethyl-1-(phenylmethyl)-1H-indol-4-yl]oxy]acetic acid

3B

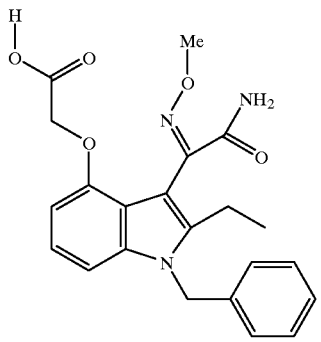

A. Preparation of 2-[[3-[[2-(Aminooxo)-1-(N-methyloxyimino)]ethyl]-2-ethyl-1-(phenylmethyl)-1H-indol-4-yl]oxy]acetic acid methyl ester Following the experimental procedure as described in Example 1 Part A, 2B was synthesized from 1 and O-methylhydroxylamine hydrochloride as a white solid in 75% yield. IR (CHCl$_3$) 3476, 3344, 1756, 1678 cm$^{-1}$; $^1$H-NMR (CDCl$_3$) δ1.18 (t, J=7.5 Hz, 3H), 2.88 (q, J=7.5 Hz, 2H), 3.83 (s, 3H), 3.99 (s, 3H), 4.71 (s, 2H), 5.31 (s, 2H), 5.60 (br s, 1H), 6.43 (d, J=7.7 Hz, 1H), 6.81 (d, J=8.2 Hz, 1H), 6.94–7.01 (m, 3H), 7.19–7.27 (m, 3H), 7.82 (br s, 1H); ESIMS m/e 424 (M$^+$+1).

Elemental Analyses for C$_{23}$H$_{25}$N$_3$O$_5$: Calculated: C, 65.24; H, 5.95; N, 9.92. Found: C, 65.13; H, 5.72; N, 9.87.

B. Preparation of 2-[[3-[[2-(Aminooxo)-1-(N-methyloxyimino)]ethyl]-2-ethyl-1-(phenylmethyl)-1H-indol-4-yl]oxy]acetic acid

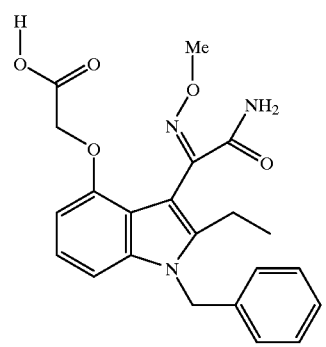

3B

Following the experimental procedure as described in Example 1 Part B, 3B was obtained as a white solid in 97% yield. IR (KBr) 3420, 3330, 3220, 1725, 1646 cm$^{-1}$; $^1$H-NMR (CDCl$_3$) δ1.19 (t, J=7.5 Hz, 3H), 2.86 (q, J 7.5 Hz, 2H), 4.03 (s, 3H), 4.72 (s, 2H), 5.34 (s, 2H), 6.53 (d, J=7.9 Hz, 1H), 6.85 (d, J=8.2 Hz, 1H), 6.99–7.05 (m, 3H), 7.23–7.32 (m, 3H), 7.53 (br s, 1H), 8.24 (br s, 1H); ESIMS m/e 410 (M$^+$+1).

Elemental Analyses for C$_{22}$H$_{23}$N$_3$O$_5$.0.70(H$_2$O): Calculated: C, 62.61; H, 5.83; N, 9.96; Found: C, 62.64; H, 5.59; N, 9.86.

EXAMPLE 3

2-[[3-[[2-(Aminooxo)-1-(N-ethyloxyimino)]ethyl]-2-ethyl-1-(phenylmethyl)-1H-indol-4-yl]oxy]acetic acid

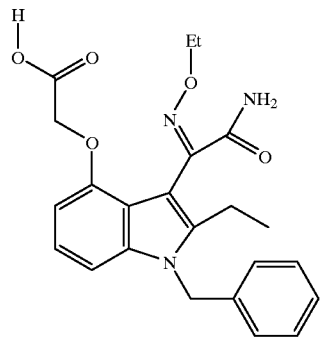

3C

A. Preparation of 2-[[3-[[2-(Aminooxo)-1-(N-ethyloxyimino)]ethyl]-2-ethyl-1-(phenylmethyl)-1H-indol-4-yl]oxy]acetic acid methyl ester

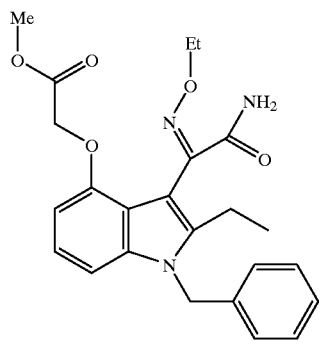

2C

Following the experimental procedure as described in Example 1 Part A, 2C was synthesized from 1 and O-ethylhydroxylamine hydrochloride as a white solid in 66% yield. IR (CHCl$_3$) 3490, 3350, 1757, 1678 cm$^{-1}$; $^1$H-NMR (CDCl$_3$) δ1.20 (t, J=7.5 Hz, 3H), 1.34 (t, J=7.0 Hz, 3H), 2.90 (q, J=7.5 Hz, 2H), 3.84 (s, 3H), 4.27 (q, J=7.0 Hz, 2H), 4.72 (s, 2H), 5.33 (s, 2H), 5.64 (br s, 1H), 6.45 (d, J 7.8 Hz, 1H), 6.84 (d, J=8.2 Hz, 1H), 6.96–7.02 (m, 3H), 7.20–7.30 (m, 3H), 7.82 (br s, 1H); ESIMS m/e 438 (M$^+$+1).

Elemental Analyses for C$_{24}$H$_{27}$N$_3$O$_5$: Calculated: C, 65.89; H, 6.22; N, 9.60; Found: C, 66.06; H, 6.34; N, 9.59.

B. Preparation of 2-[[3-[[2-(Aminooxo)-1-(N-ethyloxyimino)]ethyl]-2-ethyl-1-(phenylmethyl)-1H-indol-4-yl]oxy]acetic acid

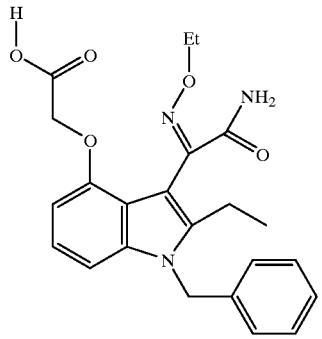

3C

Following the experimental procedure as described in Example 1 Part B, 3C was obtained as a white solid in 95% yield. IR (CHCl$_3$) 3405, 3320, 3220, 1722, 1658 cm$^{-1}$; $^1$H-NMR (CDCl$_3$) δ1.19 (t, J=7.5 Hz, 3H), 1.34 (t, J=7.0 Hz, 3H), 2.86 (q, J=7.5 Hz, 2H), 4.29 (q, J=7.0 Hz, 2H), 4.72 (s, 2H), 5.34 (s, 2H), 6.51 (d, J=7.8 Hz, 1H), 6.85 (d, J=8.2 Hz, 1H), 6.99–7.05 (m, 3H), 7.23–7.32 (m, 3H), 7.40 (br s, 1H), 8.14 (br s, 1H); ESIMS m/e 424 (M$^+$+1).

EXAMPLE 4

2-[[3-[[2-(Aminooxo)-1-(N-methyloxyimino)]ethyl]-2-ethyl-1-(phenylmethyl)-1H-indol-4-yl]oxy]acetamide

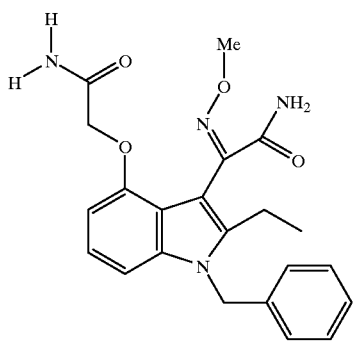

4A

Ammonia gas was bubbled through a stirred solution of 3B (98.5 mg, 0.241 mmol) and benzotriazo-1-yloxytris-(dimethylamino)phosphonium hexafluorophosphate (160 mg, 0.361 mmol) in DMF (2 mL) at ambient temperature under nitrogen. The mixture was stirred for 2 h with intermittent bubbling of ammonia gas. After concentration and subsequent chromatography on silica [gradient 0–10% CH$_3$OH in CH$_2$Cl$_2$/THF(1:1)], the title compound 4A (80.2 mg) was obtained as a white solid in 81% yield. IR (KBr) 3441, 3427, 3275, 3212, 1633 cm$^{-1}$; $^1$H-NMR (DMSO-d$_6$) δ1.03 (t, J=7.2 Hz, 3H), 2.74 (q, J=7.2 Hz, 2H), 3.81 (s, 3H), 4.47 (s, 2H), 5.41 (s, 2H), 6.42–6.46 (m, 1H), 6.92–6.96 (m, 3H), 7.18–7.29 (m, 4H), 7.41 (s, 1H), 7.52 (s, 1H), 7.61 (s, 1H), 7.91 (s, 1H); ESIMS m/e 409 (M$^+$+1).

Elemental Analyses for C$_{22}$H$_{24}$N$_4$O$_4$.0.40(CH$_3$OH): Calculated: C, 63.87; H, 6.13; N, 13.30; Found: C, 63.72; H, 6.03; N, 13.41.

EXAMPLE 5

2-[2-[[3-[[2-(Aminooxo)-1-(N-methyloxyimino)]ethyl]-2-ethyl-1-(phenylmethyl)-1H-indol-4-yl]oxy]acetamido]acetic acid

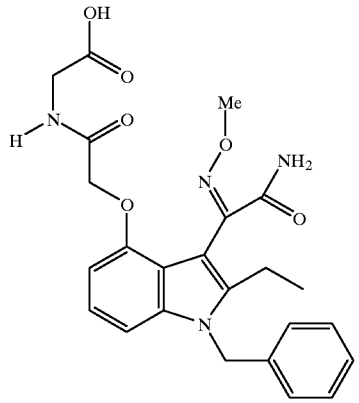

A. Preparation of 2-[2-[[3-[[2-(Aminooxo)-1-(N-methyloxyimino)]ethyl]-2-ethyl-1-(phenylmethyl)-1H-indol-4-yl]oxy]acetamido]acetic acid methyl ester

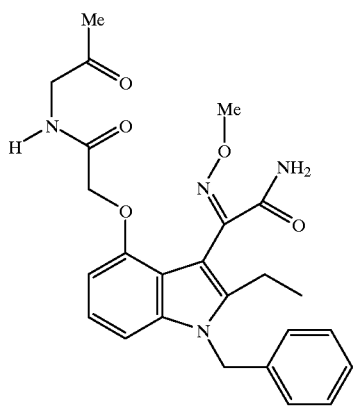

4B 2,4,6-Collidine (0.0967 mL, 0.732 mmol) was added to a stirred solution of 3B (100 mg, 0.244 mmol), glycine methyl ester hydrochloride (46.0 mg, 0.366 mmol) and benzotriazo-1-yloxytris-(dimethylamino)phosphonium hexafluorophosphate (162 mg, 0.366 mmol) in DMF (2 mL) at ambient temperature under nitrogen. The mixture was stirred for 3 h. After concentration and subsequent chromatography on silica [gradient 0–50% THF/CH$_2$Cl$_2$ (1:1)], the title compound 4B (118 mg) was obtained as a white solid in 100% yield. IR (CHCl$_3$) 3500, 3350, 3320, 1745, 1672 cm$^{-1}$; $^1$H-NMR (CDCl$_3$) δ1.18 (t, J=7.5 Hz, 3H), 2.87 (q, J=7.5 Hz, 2H), 3.73 (s, 3H), 4.04 (d, J=6.2 Hz, 2H), 4.10 (s, 3H), 4.75 (s, 2H), 5.34 (s, 2H), 6.47 (d, J=7.9 Hz, 1H), 6.83 (d, J=8.2 Hz, 1H), 6.96–7.04 (m, 3H), 7.22–7.32 (m, 4H), 7.34 (br s, 1H), 8.02 (br t, J=6.2 Hz, 1H); ESIMS m/e 481 (M$^+$+1).

Elemental Analyses for C$_{25}$H$_{28}$N$_4$O$_6$: Calculated: C, 62.49; H, 5.87; N, 11.66; Found: C, 62.78; H, 5.55; N, 12.14.

B. Preparation of 2-[2-[[3-[[2-(Aminooxo)-1-(N-methyloxyimino)]ethyl]-2-ethyl-1-(phenylmethyl)-1H-indol-4-yl]oxy]acetamido]acetic acid

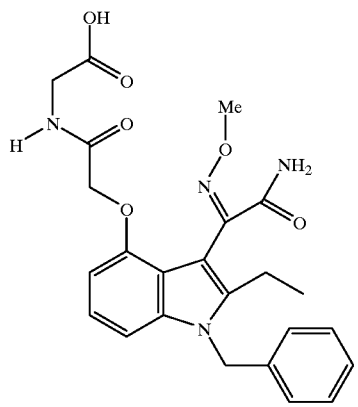

5

Following the experimental procedure as described in Example 1 Part B, 5 was obtained as a white solid in 97% yield. IR (KBr) 3415, 3400, 3000, 1767, 1665, 1633 cm$^{-1}$; $^1$H-NMR (DMSO-d$_6$) δ1.03 (t, J=7.4 Hz, 3H), 2.74 (q, J=7.4 Hz, 2H), 3.79 (s, 3H), 3.81 (d, J=6.2 Hz, 2H), 4.58 (s, 2H), 5.41 (s, 2H), 6.49 (br t, J=4.2 Hz, 1H), 6.92–6.97 (m, 4H), 7.18–7.28 (m, 3H), 7.59 (s, 1H), 7.85 (s, 1H), 8.52 (br t, J=6.2 Hz, 1H), 12.60 (br s, 1H); ESIMS m/e 467 (M$^+$+1).

Elemental Analyses for C$_{24}$H$_{26}$N$_4$O$_6$: Calculated: C, 61.79; H, 5.62; N, 12.01; Found: C, 61.91; H, 5.90; N, 11.94.

EXAMPLE 6

2-[[3-[[2-(Aminooxo)-1-(N-hydroxyimino)]ethyl]-2-ethyl-6-methyl-1-(phenylmethyl)-1H-indol-4-yl]oxy]acetic acid

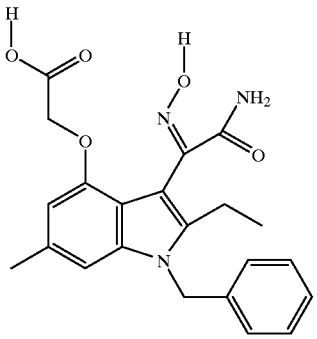

8A

A. Preparation of 2-[[3-[[2-(Aminooxo)-1-(N-hydroxyimino)]ethyl]-2-ethyl-6-methyl-1-(phenylmethyl)-1H-indol-4-yl]oxy]acetic acid methyl ester

7A

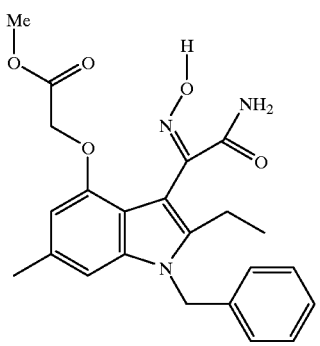

A stirred mixture of 6, 2-[[3-[[2-(Aminooxo)-1-(oxo)]ethyl]-2-ethyl-6-methyl-1-(phenylmethyl)-1H-indol-4-yl]oxy)acetic acid methyl ester, (408.5 mg, 1.0 mmol), hydroxylamine hydrochloride (421 mg, 6.0 mmol)and anhydrous sodium acetate (492 mg, 6.0 mmol) in THF (3 mL)/CH$_3$OH (3 mL) was heated at reflux temperature for 5 h. After concentration in vacuo at ambient temperature, the residue was dissolved in 10% THF/ethyl acetate, washed with H$_2$O, 1 N HCl, H$_2$O, saturated NaHCO$_3$ solution, H$_2$O, and saturated brine, dried over anhydrous magnesium sulfate, filtered, and concentrated in vacuo. The residue was purified by column chromatography on silica gel (elution with 100% EtOAc) to afford the title compound 7A (226 mg) as a white solid in 25% yield. IR (KBr, cm$^{-1}$) 3380, 3183, 1751, 1676, 1579; $^1$H-NMR (CDCl$_3$) δ1.13 (t, J=7.5 Hz, 3H), 2.34 (s, 3H), 2.79 (q, J=7.5 Hz, 2H), 3.80 (s, 3H), 4.69 (s, 2H), 5.30 (s, 2H), 5.60 (br s, 1H), 6.22 (s, 1H), 6.30 (br s, 1H), 6.66 (s, 1H), 6.97 (d, J 7.7 Hz, 2H), 7.21–7.29 (m, 4H); ESIMS m/e 424 (M$^+$+1).

Elemental Analyses for C$_{23}$H$_{25}$N$_3$O$_5$: Calculated: C, 65.24; H, 5.95; N, 9.92; Found: C, 65.27; H, 5.95; N, 9.80.

B. Preparation of 2-[[3-[[2-(Aminooxo)-1-(N-hydroxyimino)]ethyl]-2-ethyl-6-methyl-1-(phenylmethyl)-1H-indol-4-yl]oxy]acetic acid

8A

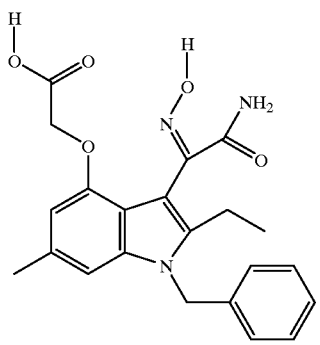

A mixture of 7A (85.0 mg, 0.2 mmol)and sodium hydroxide (1.0 N, 220 μL, 0.22 mmol) in ethanol (5.0 mL) was stirred for 1.5 h to form a colorless solution. The ethanol was removed in vacuo, the residue dissolved in water and ethyl acetate, and acidified to pH 2 with 1 N HCl. The aqueous layer was extracted twice with ethyl acetate. The combined organic extracts were washed with saturated brine, dried over magnesium sulfate, filtered, and concentrated to afford the title compound 8A (44 mg) as a white solid in 54% yield. IR (KBr, cm$^{-1}$) 3488, 3372, 2520, 1690, 1610 ; $^1$H-NMR (DMSO-d$_6$) δ1.01 (t, J=7.5 Hz, 3H), 2.27 (s, 3H), 2.67 (q, J=7.5 Hz, 2H), 4.65 (s, 2H), 5.36 (s, 2H), 6.31 (s, 1H), 6.75 (s, 1H), 6.93 (d, J=7.2 Hz, 2H), 7.17–7.28 (m, 3H), 7.52 (br s, 2H), 11.26 (s, 1H), 13.15 (br s, 1H); ESIMS m/e 410 (M$^+$+1).

Elemental Analyses for C$_{22}$H$_{23}$N$_3$O$_5$: Calculated: C, 64.54; H, 5.66; N, 10.26; Found: C, 64.73; H, 5.34; N, 10.35.

EXAMPLE 7

2-[[3-[[2-(Aminooxo)-1-(N-methyloxyimino)]ethyl]-2-ethyl-6-methyl-1-(phenylmethyl)-1H-indol-4-yl]oxy]acetic acid, sodium salt

8B

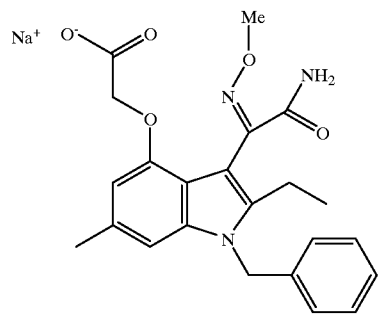

A. Preparation of 2-[[3-[[2-(Aminooxo)-1-(N-methyloxyimino)]ethyl]-2-ethyl-6-methyl-1-(phenylmethyl)-1H-indol-4-yl]oxy]acetic acid methyl ester

7B

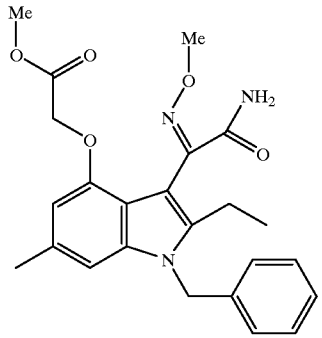

A stirred mixture of 6, 2-[[3-[[2-(Aminooxo)-1-(oxo)]ethyl]-2-ethyl-6-methyl-1-(phenylmethyl)-1H-indol-4-yl]oxy]acetic acid methyl ester, (408.5 mg, 1.0 mmol), O-methylhydroxylamine hydrochloride (501 mg, 6.0 mmol), and anhydrous sodium acetate (492 mg, 6.0 mmol) in THF (3 mL)/CH$_3$OH (3 mL) was heated at reflux temperature for 8 h. After concentration in vacuo at ambient temperature, the residue was dissolved in 10% THF/ethyl acetate, washed with H$_2$O, 1 N HCl, H$_2$O, saturated NaHCO$_3$ solution, H$_2$O, and saturated brine, dried over anhydrous magnesium sulfate, filtered, and concentrated in vacuo to afford the title compound 7B (435 mg) as a white solid in 99% yield. IR (KBr, cm$^{-1}$) 3378, 3178, 1756, 1678, 1577; $^1$H-NMR (CDCl$_3$) δ1.16 (t, J=7.5 Hz, 3H), 2.33 (s, 3H), 2.84 (q, J=7.5 Hz, 2H), 3.84 (s, 3H), 3.99 (s, 3H), 4.69 (s, 2H), 5.28 (s, 2H), 5.58 (br s, 1H), 6.27 (s, 1H), 6.63 (s, 1H), 6.98 (d, J=6.3 Hz, 2H), 7.19–7.27 (m, 3 H), 7.80 (br s, 1H); ESIMS m/e 438 (M$^+$+1).

Elemental Analyses for C$_{24}$H$_{27}$N$_3$O$_5$: Calculated: C, 65.89; H, 6.22; N, 9.60; Found: C, 66.16; H, 6.27; N, 9.68.

B. Preparation of 2-[[3-[[2-(Aminooxo)-1-(N-methyloxyimino)]ethyl]-2-ethyl-6-methyl-1-(phenylmethyl)-1H-indol-4-yl]oxy]acetic acid, sodium salt

8B

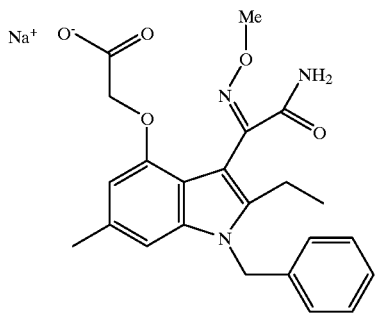

A suspension of 7B (88.0 mg, 0.2 mmol)and sodium hydroxide (1.0 N, 220 μL, 0.22 mmol) in ethanol (5.0 mL) was stirred for 0.5 h to form a hazy solution, and after 1.0 h a thick white precipitate had formed. After 3.0 h total stirring the resultant white precipitate was collected by filtration, washed with small amounts of EtOH, diethyl ether, and hexanes, then dried in vacuo to afford the title compound 8B (84 mg) as a white solid in 94% yield. IR (KBr, cm$^{-1}$) 3353, 3230, 1667, 1604; $^1$H-NMR (DMSO-d$_6$) δ1.03 (t, J=7.5 Hz, 3H), 2.27 (s, 3H), 2.65 (q, J=7.5 Hz, 2H), 3.75 (s, 3H), 4.05 (s, 2H), 5.33 (s, 2H), 6.26 (s, 1H), 6.66 (s, 1H), 6.92 (d, J=7.2 Hz, 2H), 7.01 (br s, 1H), 7.19–7.27 (m, 3H), 10.11 (br s, 1H); ESIMS m/e 424 (M++1 carboxylic acid).

Elemental Analyses for $C_{23}H_{24}N_3NaO_5$: Calculated: C, 62.02; H, 5.43; N, 9.43; Found: C, 64.57; H, 5.68; N, 9.85.

Assay

The following chromogenic assay procedure was used to identify and evaluate inhibitors of recombinant human secreted phospholipase A$_2$. The assay described herein has been adapted for high volume screening using 96 well microtiter plates. A general description of this assay method is found in the article, "Analysis of Human Synovial Fluid Phospholipase A$_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis,*Analytical Biochemistry*, 204, pp. 190–197, 1992 (the disclosure of which is incorporated herein by reference):

Reagents
Reaction Buffer

| | |
|---|---|
| CaCl$_2$.2H$_2$O | (1.47 g/L) |
| KCl | (7.455 g/L) |

Bovine Serum Albumin (fatty acid free) (1 g/L)
(Sigma A-7030, product of Sigma Chemical Co., St. Louis Mo., USA)

| | |
|---|---|
| TRIS HCl | (3.94 g/L) | pH 7.5 (adjust with NaOH)

Enzyme Buffer
0.05 NaOAc.3H$_2$O, pH 4.5
0.2 NaCl
Adjust pH to 4.5 with acetic acid
DTNB—5,5'-dithiobis-2-nitrobenzoic acid
Racemic Diheptanoyl Thio-PC
racemic 1,2-bis(heptanoylthio)-1,2-dideoxy-glycero-3-phosphorylcholine
TRITON X-100™ prepare at 6.249 mg/ml in reaction buffer to equal 10 uM.

Reaction Mixture

A measured volume of racemic dipheptanoyl thio PC supplied in chloroform at a concentration of 100 mg/ml is taken to dryness and redissolved in 10 millimolar TRITON X-$_{100}$™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:
1. Add 0.2 ml reaction mixture to all wells;
2. Add 10 ul test compound (or solvent blank) to appropriate wells, mix 20 seconds;
3. Add 50 nanograms of sPLA$_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, IC$_{50}$ values were determined. Typically, the IC$_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of ICso values. IC$_{50}$ were determined by plotting log concentration versus inhibition values in the range from 10–90% inhibition.

Results of Human Secreted Phospholipase A$_2$ Inhibition Tests

TABLE

| Compound of Example No. | Inhibition of human secreted PLA$_2$ IC50 ± mean deviation (3–4 tests) |
|---|---|
| 1 | 49nM |

The compound of Example 1 is highly active in inhibiting sPLA$_2$.

While the present invention has been illustrated above by certain specific embodiments, it is not intended that these specific examples should limit the scope of the invention as described in the appended claims.

We claim:

1. An indole compound represented by the formula (I), or a pharmaceutically acceptable salt, solvate, or prodrug derivative thereof;

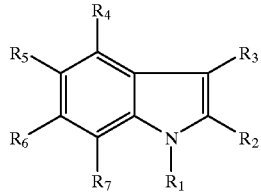

(I)

wherein $R_1$ is selected from groups (a), (b) and (c) wherein;
(a) is $C_7$–$C_{20}$ alkyl, $C_7$–$C_{20}$ haloalkyl, $C_7$–$C_{20}$ alkenyl, $C_7$–$C_{20}$ alkynyl, carbocyclic radical, or heterocyclic radical,
(b) is a member of (a) substituted with one or more independently selected non-interfering substituents; and
(c) is the group —($L_1$)—$R_{11}$; where, —($L_1$)— is a divalent linking group of 1 to 8 atoms and $R_{11}$ is a group selected from (a) or (b);

$R_2$ is hydrogen, $C_1$–$C_4$ alkyl, $C_2$–$C_4$ alkenyl, —O—($C_1$–$C_3$ alkyl), —S—($C_1$–$C_3$ alkyl), —$C_3$–$C_4$ cycloalkyl —$CF_3$, halo, —$NO_2$, —CN, or —$SO_3$;

$R_3$ is —($L_3$)—Z, where —($L_3$)— is a bond or a divalent group selected from:

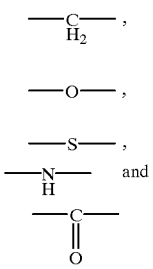

and Z is a oxime amide or oxime thioamide group represented by the formulae,

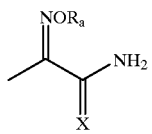

where

X is oxygen or sulfur; and $R_a$ is selected from hydrogen, $C_1$–$C_8$ alkyl, aryl, $C_1$–$C_8$ alkaryl, $C_1$–$C_8$ alkoxy, $C_1$ to $C_8$ aralkyl and —CN;

$R_4$ and $R_5$ each independently selected from hydrogen, a non-interfering substituent, or the group, —($L_a$)-(acidic group), where —($L_a$)—, is a divalent acid linker, wherein the acid linker group, —(La)—, for $R_4$ is the group:

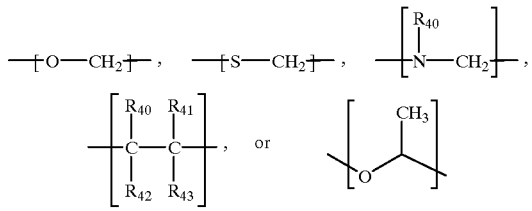

where $R_{40}$, $R_{41}$, $R_{42}$, and $R_{43}$ are each independently selected from hydrogen, $C_1$–$C_8$ alkyl, and wherein the acid linker group, —(La)—, for $R_5$ is selected from the group consisting of

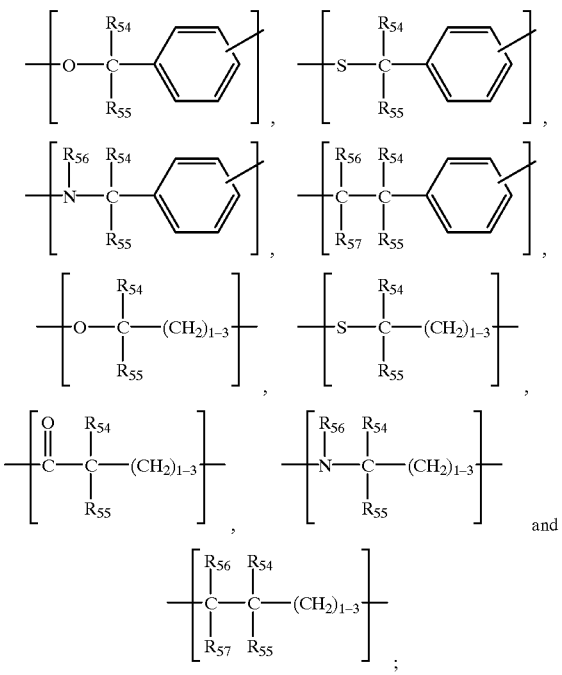

wherein $R_{54}$, $R_{55}$, $R_{56}$ and $R_{57}$ are each independently hydrogen, $C_1$–$C_8$ alkyl, $C_1$–$C_8$ haloalkyl, aryl, $C_1$–$C_8$ alkoxy, or halo;

$R_6$ and $R_7$ are each independently selected from hydrogen, non-interfering substituent, carbocyclic radical, carbocyclic radical substituted with non-interfering substituent(s), heterocyclic radical, and heterocyclic radical substituted with non-interfering substituent(s);

provided that at least one of $R_4$ and $R_5$ must be the group, —($L_a$)-(acidic group); and provided that the non-interfering substituent(s) of $R_1$, $R_4$, $R_5$, $R_6$ and $R_7$ is independently selected from hydrogen, $C_1$–$C_8$ alkyl, $C_2$–$C_8$ alkenyl, $C_2$–$C_8$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_8$ alkoxy, $C_2$–$C_8$ alkenyloxy, $C_2$–$C_8$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_8$ alkylsulfinyl, $C_1$–$C_8$ alkylsulfonyl, $C_2$–$C_8$ haloalkoxy, $C_1$–$C_8$ haloalkylsulfonyl, $C_2$–$C_8$ haloalkyl, $C_1$–$C_8$ hydroxyalkyl, —C(O)O($C_1$–$C_8$ alkyl), —($CH_2$)$_n$—O—($C_1$–$C_8$ alkyl), benzyloxy, phenoxy, phenylthio, —(CONHSO$_2$R), —CHO, amino, amidino, bromo, carbamyl, carboxyl, carbalkoxy, —($CH_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, or carbonyl; where n is from 1 to 8; and provided that the (acidic group) of $R_4$ and $R_5$ is the group:

-5-tetrazolyl,

—SO$_3$H,

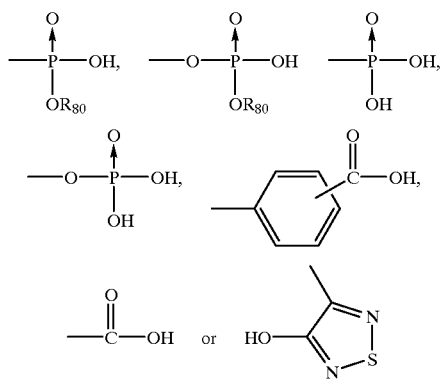

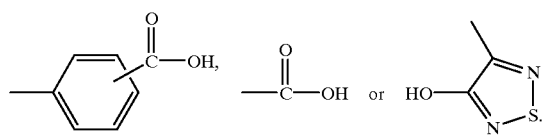

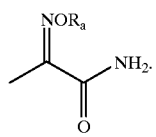

where $R_{80}$ is a metal or $C_1$–$C_8$ alkyl.

2. The compound of claim 1 wherein only one of $R_4$ and $R_5$ is the group, —($L_a$)-(acidic group) and wherein the (acidic group) is the group:

-5-tetrazolyl,

—SO$_3$H,

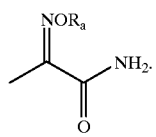

3. The compound of claim 2 wherein the acidic group is —CO$_2$H.

4. The compound of claim 1 wherein for $R_3$, Z is the group represented by the formula;

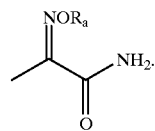

and the linking group —($L_3$)— is a bond; and $R_a$ is hydrogen, methyl, ethyl, propyl, isopropyl, phenyl or benzyl.

5. The compound of claim 1 wherein for $R_3$, Z is the group represented by the formula;

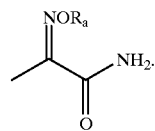

and the linking group —($L_3$)— is a bond; and $R_a$ is hydrogen.

6. The compound of claim 1 wherein for $R_3$, Z is the group represented by the formula;

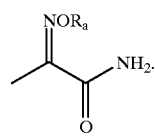

and the linking group —($L_3$)— is a bond; and $R_a$ is methyl, ethyl, propyl, isopropyl, phenyl or benzyl.

7. The compound of claim 1 wherein for $R_1$ the divalent linking group —($L_1$)— is selected from a group represented by the formulae (Ia), (Ib), (Ic), (Id), (Ie), and (If):

 (Ia)

 (Ib)

 (Ic)

 (Id)

 (Ie)

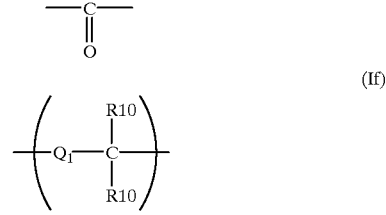 (If)

where $Q_1$ is a bond or any of the divalent groups Ia, Ib, Ic, Id, and Ie and $R_{10}$ is independently —H, $C_{1-8}$ alkyl, $C_{1-8}$ haloalkyl or $C_{1-8}$ alkoxy.

8. The compound of claim 1 wherein the linking group —($L_1$)— of $R_1$ is —(CH$_2$)— or —(CH$_2$—CH$_2$)—.

9. The compound of claim 1 wherein for $R_1$, the group $R_{11}$ is a substituted or unsubstituted carbocyclic radical selected from the group consisting of cycloalkyl, cycloalkenyl, phenyl, spiro[5.5]undecanyl, naphthyl, norbornanyl, bicycloheptadienyl, tolulyl, xylenyl, indenyl, stilbenyl, terphenylyl, diphenylethylenyl, phenyl-cyclohexenyl, acenaphthylenyl, anthracenyl, biphenyl, bibenzylyl and related bibenzylyl homologues represented by the formula (a):

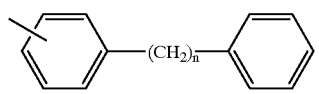

(a)

where n is a number from 1 to 8.

10. The compound of claim 7 wherein for $R_1$ the combined group $-(L_1)-R_{11}$ is;

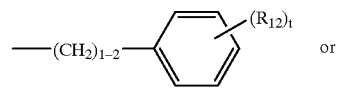

or

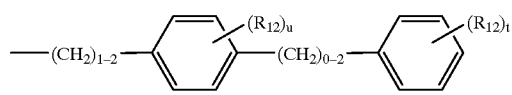

where $R_{12}$ is a radical independently selected from halo, $C_1-C_{10}$ alkyl, $C_1-C_{10}$ alkoxy, $-S-(C_1-C_{10}$ alkyl), $C_1-C_{10}$ haloalkyl, and $C_1-C_{10}$ hydroxyalkyl; t is a number from 0 to 5 and u is a number from 0 to 4.

11. The compound of claim 1 wherein for $R_1$ the radical $R_{11}$ is a substituted or unsubstituted heterocyclic radical selected from pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, benzotriazolyl, anthranilyl, 1,2-benzisoxazolyl, benzoxazolyl, benzothiazolyl, purinyl, pyridinyl, dipyridylyl. phenylpyridinyl, benzylpyridinyl, pyrimidinyl, phenylpyrimidinyl, pyrazinyl, 1,3,5-triazinyl, quinolinyl, phthalazinyl, quinazolinylmorpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiopheneyl, pentamethylenesulfadyl, 1,3-dithianyl, 1,4-dithianyl, 1,4-thioxanyl, azetidinyl, hexamethyleneiminium, heptamethyleneiminium, piperazinyl or quinoxalinyl.

12. The compound of claim 1 in the form of a sodium salt.

13. The compound of claim 1 in the form of an ester prodrug.

14. An indole compound represented by the formula (II), or a pharmaceutically acceptable salt, solvate, or prodrug derivative thereof;

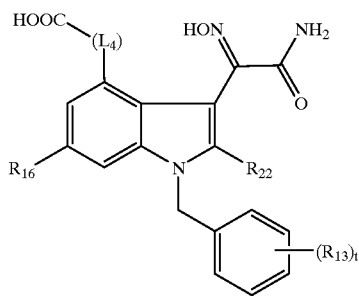

(II)

wherein;

$R_{22}$ is hydrogen, methyl, ethyl, propyl, isopropyl, cyclopropyl, —F, —$CF_3$, —Cl, —Br, or —O—$CH_3$;

—($L_4$)— is a divalent group selected from;

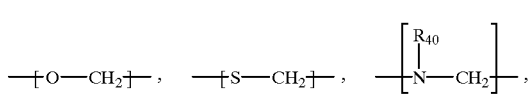

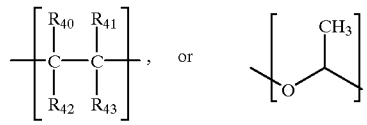

where $R_{40}$, $R_{41}$, $R_{42}$, and $R_{43}$ are each independently selected from hydrogen or $C_1-C_8$ alkyl;

$R_{16}$ is selected from hydrogen, $C_1-C_8$ alkyl, $C_1-C_8$ alkoxy, $C_1-C_8$ alkylthio $C_1-C_8$ haloalkyl, $C_1-C_8$ hydroxyalkyl, and halo;

$R_{13}$ is selected from hydrogen, $C_1-C_8$ alkyl, $C_1-C_8$ alkoxy, —S—($C_1-C_8$ alkyl), $C_1-C_8$ haloalkyl, $C_1-C_8$, phenyl, halophenyl, hydroxyalkyl, and halo, and t is an integer from 0 to 5.

15. An indole compound represented by the formulae (C1) or (C2);

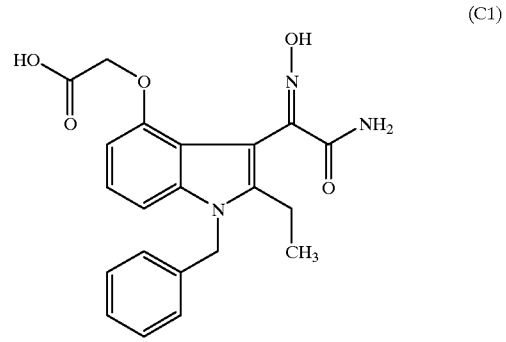

(C1)

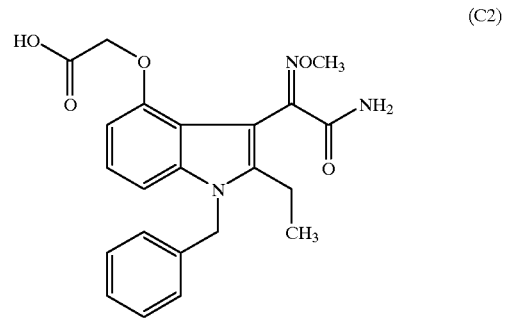

(C2)

or a pharmaceutically acceptable salt or prodrug thereof.

16. An indole compound represented by the formulae (C1), (C2) or (C3);

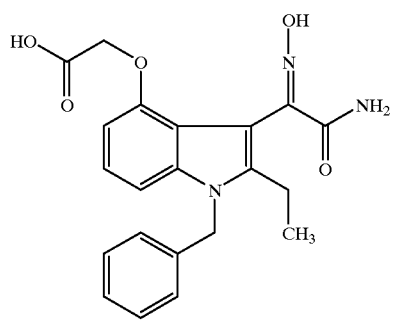

(C1)

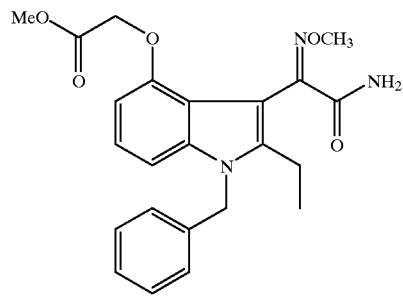

(C3)

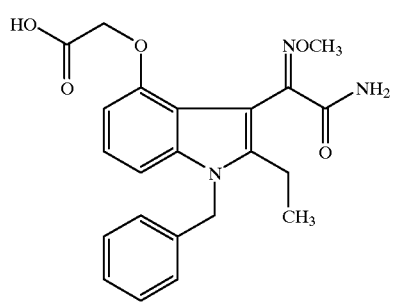

(C2)

or a pharmaceutically acceptable salt or prodrug thereof.

17. A pharmaceutical formulation comprising a therapeutically effective amount of an indole compound as claimed in claim 1 together with a pharmaceutically acceptable carrier or diluent therefor.

18. A method of inhibiting sPLA$_2$ mediated release of fatty acid which comprises contacting sPLA$_2$ with a therapeutically effective amount of indole compound as claimed in claim 1.

19. A method of treating a mammal to alleviate the pathological effects of Inflammatory Diseases; wherein the method comprises administration to said mammal of at least one indole compound as claimed in claim 1 in a pharmaceutically effective amount.

\* \* \* \* \*